US00PP21319P2

(12) United States Plant Patent
van Waaij

(10) Patent No.: US PP21,319 P2
(45) Date of Patent: Sep. 28, 2010

(54) *BUXUS* PLANT NAMED 'FURORE'

(50) Latin Name: *Buxus sempervirens*
Varietal Denomination: Furore

(76) Inventor: Jan Cornelis van Waaij, Burgmeester Smitweg 112, Hazerswoude-Dorp (NL) 2391 NG ( * ) Notice: Subject to any disclaimer, the term of this patent is extended or adjusted under 35 U.S.C. 154(b) by 0 days.

(21) Appl. No.: 12/454,590

(22) Filed: May 20, 2009

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

*Buxus sempervirens* Jade Pillar, [retrieved on Apr. 22, 2010]. Retrieved from the Internet: <www.ballhort.com/Nursery/plant_info.aspz?phid=111600001023912> 2 pp.*

* cited by examiner

*Primary Examiner*—June Hwu
(74) *Attorney, Agent, or Firm*—Audrey Charles

(57) ABSTRACT

A new and distinct cultivar of *Buxus* plant named 'Furore', characterized by its upright narrow-pyramidal growth habit, dense dark green-colored foliage, and good garden performance.

2 Drawing Sheets

Latin name of genus and species of plant claimed: *Buxus sempervirens.*

Variety denomination: 'Furore'.

BACKGROUND OF THE INVENTION

The present invention relates to a new and distinct cultivar of *Buxus* plant botanically known as *Buxus sempervirens* and hereinafter referred to by the cultivar name 'Furore'.

The new *Buxus* cultivar is a naturally-occurring sport of a species plant of *Buxus sempervirens*. The species is characterized as a slow growing round-shaped evergreen shrub. It makes an excellent hedge and is very tolerant of cutting and often used in topiary, for ornamental effect. The new cultivar was discovered in 2005 as a branch mutation in an outdoor nursery location in Hazerswoude-Dorp, The Netherlands.

Asexual reproduction of the new *Buxus* by cuttings in a controlled environment in Hazerswoude-Dorp, The Netherlands since 2006, has shown that the unique features of this new *Buxus* are stable and reproduced true to type in successive generations.

SUMMARY OF THE INVENTION

The following characteristics of the new cultivar have been repeatedly observed and can be used to distinguish 'Furore' as a new and distinct cultivar of *Buxus* plant:

1. Upright narrow-pyramidal growth habit;
2. Dense dark green-colored foliage; and
3. Good garden performance.

Plants of the new cultivar differ from plants of the parent species primarily in growth habit.

Of the many commercially available *Buxus* cultivars, the most similar in comparison to the new cultivar is the cultivar 'Faulkner', not patented. However, in comparison, plants of the new cultivar differ from plants of 'Faulkner' primarily in internode length. Plants of 'Furore' have shorter internodes compared with plants of 'Faulkner'. Having shorter internodes makes for a stronger plant that maintains a desired shape in the garden.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Furore'. The plants were grown outdoors in containers for approximately 2 years in Boskoop, The Netherlands.

The photograph on the first sheet is a side perspective view of typical plants of 'Furore' grown in a container in an outdoor nursery.

The photograph on the first second sheet is a close-up view of typical foliage of 'Furore'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in August 2008 under natural light conditions in Boskoop, The Netherlands when day temperatures ranged from 12° C. to 32° C. (53° F. to 90° F.) and night temperatures ranged from 5° C. to 16° C. (41° F. to 61° F.).

Plants used in the following description were grown in Boskoop, The Netherlands, in an outdoor nursery in containers and under conditions which closely approximate commercial production conditions. The plants were grown for approximately 2 years when the description was taken. Measurements and numerical values represent averages of typical plants.

Botanical classification: *Buxus sempervirens* cultivar Furore.

Parentage: Sport of a species plant of *Buxus sempervirens*.

Propagation:

*Type.*—Cutting.

*Time to initiate roots.*—Approximately 20 days at temperatures of approximately 20° to 25° C.

*Time to produce a rooted plant.*—Approximately 25 days at temperatures of approximately 20° to 25° C.

*Root description.*—White in color, medium thickness, fleshy.

*Rooting habit.*—Dense, freely branching.

Plant description:

*Growth habit and general appearance.*—Perennial shrub with moderate growth rate, moderate vigor, and upright narrow-pyramidal growth habit.

*Crop time.*—Approximately 12 months from an unrooted cutting to finish in an 11 cm container.

*Size.*—Plant height: Approximately 35.9 cm. Plant width (spread): Approximately 20.1 cm.

*Branching habit.*—Freely basal branching. Pinching not required, but will improve basal branching. Quantity: Approximately 7 main branches from the base with a total of 42 lateral branches.

*Lateral branches.*—Strength: Very strong. Shape: Quadrangular with rounded edges. Length: Approximately 7.4 cm. Diameter: Approximately 2.0 mm. Internode length: Approximately 1.1 cm. Texture: Glabrous. Color of young stems: 144A. Color of mature stems: 156A to 199D.

Foliage description:

*General description.*—Quantity of leaves per main stem: Approximately 14. Fragrance: None detected. Form: Simple. Arrangement: Opposite.

*Leaves.*—Shape: broad ovate to broad elliptic, slightly convexed. Appearance: Glossy. Margin: Entire. Apex: Retuse. Base: Acuminate. Venation pattern: Pinnate. Length of mature leaf: Approximately 2.3 cm. Width of mature leaf: Approximately 1.4 cm. Texture of upper and lower surfaces: Glabrous. Color of upper surface of young foliage: 144A. Color of lower surface of young foliage: 144B. Color of upper surface of mature foliage: Between 137A and 139A with venation of 143A. Color of lower surface of mature foliage: Between 143A and 144A with venation of 145B.

*Petiole.*—Length: Approximately 3.0 mm. Width: Approximately 1.0 mm. Texture: Glabrous. Color: 144A.

Flower and seed production: Not available, flower and seed production have not been observed.

Disease and pest resistance: Plants of the new *Buxus* have not been noted to be resistant to pathogens and pests common to *Buxus*.

Weather tolerance: Plants of the new *Buxus* have been observed to be hardy to a least USDA Zone 5b and tolerate temperatures to at least Zone 8.

What is claimed is:

1. A new and distinct cultivar of *Buxus* plant named 'Furore', substantially as herein shown and described.

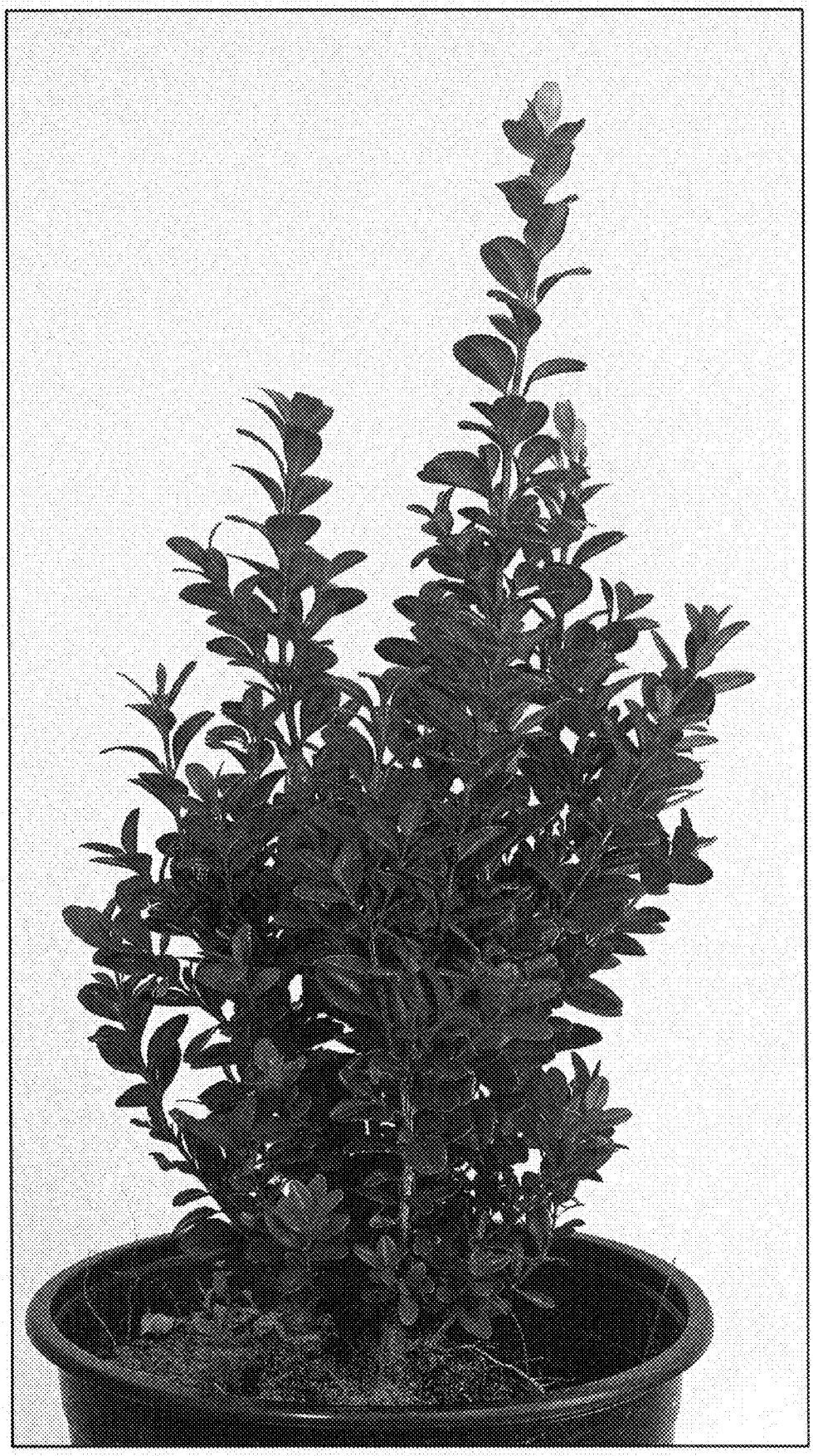

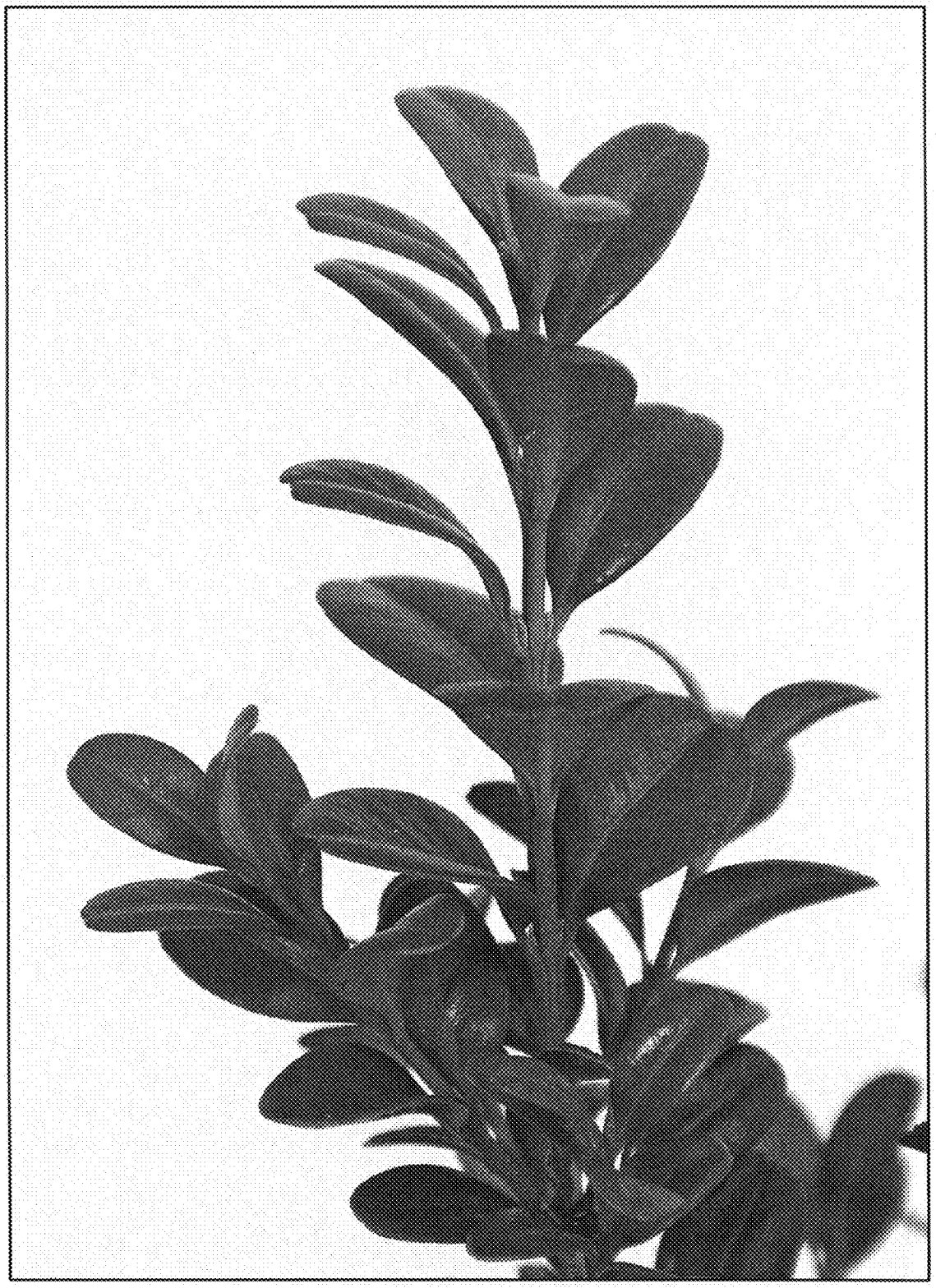

* * * * *